(12) United States Patent
Milliken et al.

(10) Patent No.: US 11,278,435 B2
(45) Date of Patent: Mar. 22, 2022

(54) RECONFIGURABLE ELECTRICAL CIRCUIT FOR SUPPLYING INCREASED POWER FROM A SUPERCAPACITOR AND METHOD FOR USING THE SAME

(71) Applicant: OTTO BOCK HEALTHCARE LP, Austin, TX (US)

(72) Inventors: Jamie Milliken, Carlisle, MA (US); Ashish Shah, Chelmsford, MA (US)

(73) Assignee: OTTO BOCK HEALTHCARE LP, Austin, TX (US)

( * ) Notice: Subject to any disclaimer, the term of this patent is extended or adjusted under 35 U.S.C. 154(b) by 0 days.

(21) Appl. No.: 16/733,541

(22) Filed: Jan. 3, 2020

(65) Prior Publication Data
US 2021/0205102 A1 Jul. 8, 2021

(51) Int. Cl.
*A61F 2/66* (2006.01)
*H02J 7/00* (2006.01)
*H02J 7/34* (2006.01)
*A61F 2/70* (2006.01)

(52) U.S. Cl.
CPC .............. *A61F 2/6607* (2013.01); *A61F 2/70* (2013.01); *H02J 7/0063* (2013.01); *H02J 7/342* (2020.01); *H02J 7/345* (2013.01); *A61F 2002/701* (2013.01); *A61F 2002/708* (2013.01); *H02J 2207/20* (2020.01)

(58) Field of Classification Search
CPC .......... H02J 7/345; H02J 7/0063; H02J 7/342; H02J 2207/20; A61F 2002/701; A61F 2002/708

USPC .......................................................... 320/167
See application file for complete search history.

(56) References Cited

U.S. PATENT DOCUMENTS

| | | | | |
|---|---|---|---|---|
| 4,255,782 A * | 3/1981 | Joyce | ..................... | H02M 5/293 363/159 |
| 6,075,331 A * | 6/2000 | Ando | ...................... | H02J 7/345 318/376 |
| 6,798,175 B2 * | 9/2004 | Hanada | .................. | H02J 7/0031 320/166 |
| 6,998,822 B2 * | 2/2006 | Turner | .................... | H02J 7/345 320/166 |
| 7,085,123 B2 * | 8/2006 | Shiue | ........................ | H02P 7/28 361/301.2 |
| 7,230,352 B2 * | 6/2007 | Bedard | ................... | H02J 7/345 307/59 |

(Continued)

Primary Examiner — M Baye Diao
(74) Attorney, Agent, or Firm — Kacvinsky Daisak Bluni PLLC

(57) ABSTRACT

Exemplary embodiments relate to techniques for supplying increased power to an augmentation device without increasing battery size. For example, the load may be a motor that provides augmentation power to a joint of a prosthetic ankle, and which is generally powered by a battery. A reconfigurable electrical circuit may connect a supercapacitor in series with the battery to boost the power from the battery at times when a pulse of increased power is demanded. For instance, states of one or more switches of the electrical circuit may be changed in order to briefly disconnect the motor from the circuit just prior to a powered plantarflexion phase of a gait cycle of the ankle, and then to reconnect the motor to a reconfigured circuit to provide a power boost. The circuit may also be reconfigured to allow the battery to recharge the supercapacitor during periods of nominal power demand.

12 Claims, 7 Drawing Sheets

(56) References Cited

U.S. PATENT DOCUMENTS

| | | | | |
|---|---|---|---|---|
| 7,969,121 | B2 * | 6/2011 | Smith | H02M 3/1584 |
| | | | | 320/167 |
| 8,179,103 | B2 * | 5/2012 | Doljack | H02J 7/345 |
| | | | | 320/166 |
| 9,143,003 | B2 * | 9/2015 | Baarman | H02J 7/025 |
| 9,889,058 | B2 * | 2/2018 | Horst | A61H 3/00 |
| 10,491,020 | B2 * | 11/2019 | Minnickel | H02J 7/00712 |
| 10,596,909 | B2 * | 3/2020 | Choi | B60L 50/40 |
| 10,980,698 | B2 * | 4/2021 | Goffer | B25J 9/0006 |
| 2010/0079109 | A1 * | 4/2010 | Eilertsen | H02J 3/32 |
| | | | | 320/127 |
| 2010/0148582 | A1 * | 6/2010 | Carter | H02J 7/1407 |
| | | | | 307/48 |

\* cited by examiner

| WALKING STATE | | | | | | |
|---|---|---|---|---|---|---|
| 1. CONTROLLED PLANTAR FLEXION | 2. CONTROLLED DORSIFLEXION | 3. POWERED PLANTAR FLEXION | 4. EARLY SWING | 5. LATE SWING | | |
| 302 | 306 | 310 | 314 | 318 | | |
| PHASE | STANCE | | | SWING | | |
| % OF CYCLE | 60% | | | 40% | | |
| INITIATING EVENT | FOOT-STRIKE | FOOT-FLAT | MAXIMUM DORSIFLEXION | TOE-OFF | VERTICAL ANKLE VELOCITY IS APPROXIMATELY ZERO | |
| FUNCTION | IMPEDANCE (SPRING-DOMINATED) | TORQUE SOURCE + NONLINEAR IMPEDANCE | TORQUE SOURCE + IMPEDANCE | POSITION CONTROL | LINEAR SPRING | |

FIG. 3

RECONFIGURABLE ELECTRICAL CIRCUIT FOR SUPPLYING INCREASED POWER FROM A SUPERCAPACITOR AND METHOD FOR USING THE SAME

FIELD OF THE INVENTION

The present application relates to improvements in power supply for augmentation devices, and in particular a reconfigurable electrical circuit for providing power from a supercapacitor to a load in a powered human prosthesis, orthosis, exoskeleton, or the like.

BACKGROUND

Powered augmentation devices may be used to replace a limb or augment its power. Examples of such devices include prosthetics, orthotics, and exoskeletons. In a powered augmentation device, power is typically provided by an actuator, which applies force or torque at appropriate times as defined by the biomechanics of the limb being augmented or replaced or by the requirements of a task.

A typical joint in an augmentation device consists of a proximal structure and a distal structure joined by a pivot. The pivot either replaces or coincides with an anatomical joint, and the proximal and distal structures of the augmentation device replace or coincide with the proximal and distal anatomy on either side of the anatomical joint. For example, in an elbow orthosis the pivot would coincide with the elbow joint and the proximal and distal structures of the device would attach to the upper and lower arm of the user. As another example, in an ankle-foot prosthesis, the pivot would replace the ankle joint and the proximal and distal structures of the device would replace all or part of the lower leg and foot. The proximal and distal structures of the augmentation device may comprise multiple parts and may include other pivots or flexible members. Typically, an actuator is disposed between the proximal and distal structures such that it can create a force or torque between them, or cause them to rotate relative to each other at the pivot.

FIG. 1A illustrates one example of a powered augmentation device in the form of an actuated prosthetic ankle. Such joints are typically arranged with an actuator 104 bridging two halves of the joint 106-1, 106-2. The respective halves of the joint 106-1, 106-2 respectively connect to a foot member 102 and a shank member 104. An interface 108 at a top end of the shank member 104 allows the prosthetic ankle to be connected to a corresponding interface fixed to a user's leg.

The actuator 104 of such designs may take the form of a screw (usually a ball screw or lead screw) and a belt or gear transmission connecting the screw to an electric motor, or a hydraulic linear actuator. The driving force (an electric motor for the actuator 104 is an example of a load that requires input electrical power, which is generally supplied by a battery 112 (see FIG. 1B). The amount and timing of the application of the power may be controlled by a controller 110.

SUMMARY

Exemplary embodiments relate to methods and systems pertaining to powered human augmentation devices, such as prosthetics, orthotics, or exoskeletons. The device may be used to replace or supplement a human limb and/or joint, such as a hip, wrist, elbow, shoulder, knee, or ankle joint, a foot, ankle, leg, hand, arm, or torso, or any combination thereof.

The powered human augmentation device may include a load, a battery configured to supply power to the load, and a supercapacitor. An electrical circuit may connect the battery, the supercapacitor, and the load.

A supercapacitor is an electrical energy storage device which charges and discharges quickly and is lightweight. Supercapcitors can have a specific power (maximum power output divided by mass) in excess of 5 times that of a battery. The use of supercapcitors can be highly advantageous when short bursts of power are required in an electrical device, and particularly advantageous when minimizing weight is an important design criteria.

The electrical circuit may be configurable in a first configuration a first configuration in which the battery and the supercapacitor jointly supply power to the load. The electrical circuit may further be configurable in a second configuration in which the battery supplies power to the load and recharges the supercapacitor. Other configurations, such as a third configuration in which the battery provides power to the load but does not recharge the supercapacitor, and a fourth configuration in which neither the battery nor the supercapacitor provide power to the load, are also contemplated.

A hardware controller may be configured to monitor signals indicative of requirements on the load, and to switch the electrical circuit between the first configuration and the second configuration (and/or the third and fourth configurations) in response to the monitored signals.

In a second embodiment, the load may be configured to alternate between a nominal power draw and receiving pulses of high power throughout a cycle associated with the powered augmentation device, and the supercapacitor may be configured to provide the pulses of high power.

A third embodiment, which may be employed in combination with any of the previously-described embodiments, may utilize a supercapacitor configured to provide 6.0 J of energy within about a 300 ms window, more preferably within a 200 ms time window, and most preferably within a 100 ms time window.

A fourth embodiment, which may employed in combination with any of the previously-described embodiments, may further include a DC/DC converter configured to convert a source voltage from the battery into a voltage level suitable for charging the supercapacitor.

A fifth embodiment, which may employed in combination with any of the previously-described embodiments, may further include multiple of field effect transistor (FET) switches. The controller may be configured to switch the electrical circuit between the first configuration and the second configuration by adjusting the FET switches.

In a sixth embodiment, which may be employed in combination with any of the previously-described embodiments, the controller may be configured to switch the electrical circuit between the first configuration and the second configuration in a period of time while the load is disconnected from the electrical circuit.

In a seventh embodiment, which may be employed in combination with any of the previously-described embodiments, the electrical circuit may be configured not to provide backflow energy from the load to the supercapacitor.

In an eighth embodiment, which may be employed in combination with any of the previously-described embodiments, the device may include an ankle, and the controller may be configured to place the electrical circuit in the first configuration from just prior to a powered plantarflexion phase of a gait cycle of the ankle until an end of the powered plantarflexion phase. In some embodiments, a sensor may detect an angle of an ankle joint, and the controller may place the electrical circuit in the first configuration based on angle measurements received from the sensor. In further embodiments, the device may include a hard stop that prevents the ankle from rotating past a certain point. When the hard stop is reached, the load may be disconnected.

In a ninth embodiment, which may employed in combination with any of the previously-described embodiments, the supercapacitor may be recharged between successive steps of the gait cycle.

These and other embodiments will next be described with reference to the attached drawings.

BRIEF DESCRIPTION OF THE DRAWINGS

FIG. 3 is a diagram illustrating various stages of a gait cycle for a human ankle.

DETAILED DESCRIPTION OF EXAMPLE EMBODIMENTS

Figure 1A:
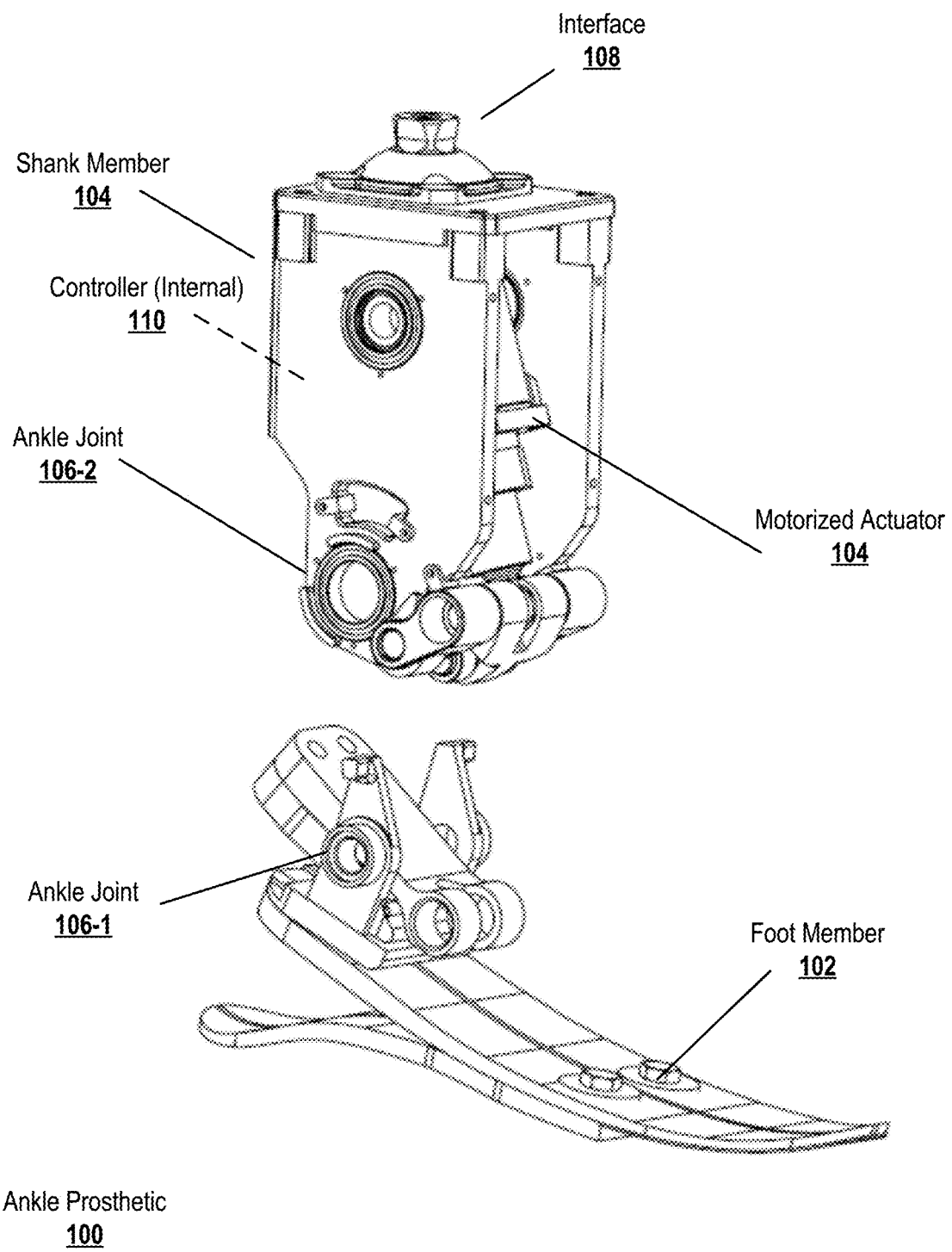
FIGS. 1A and 1B depict exemplary powered ankle-foot prostheses suitable for use in an exemplary embodiment.
Figure 1B:
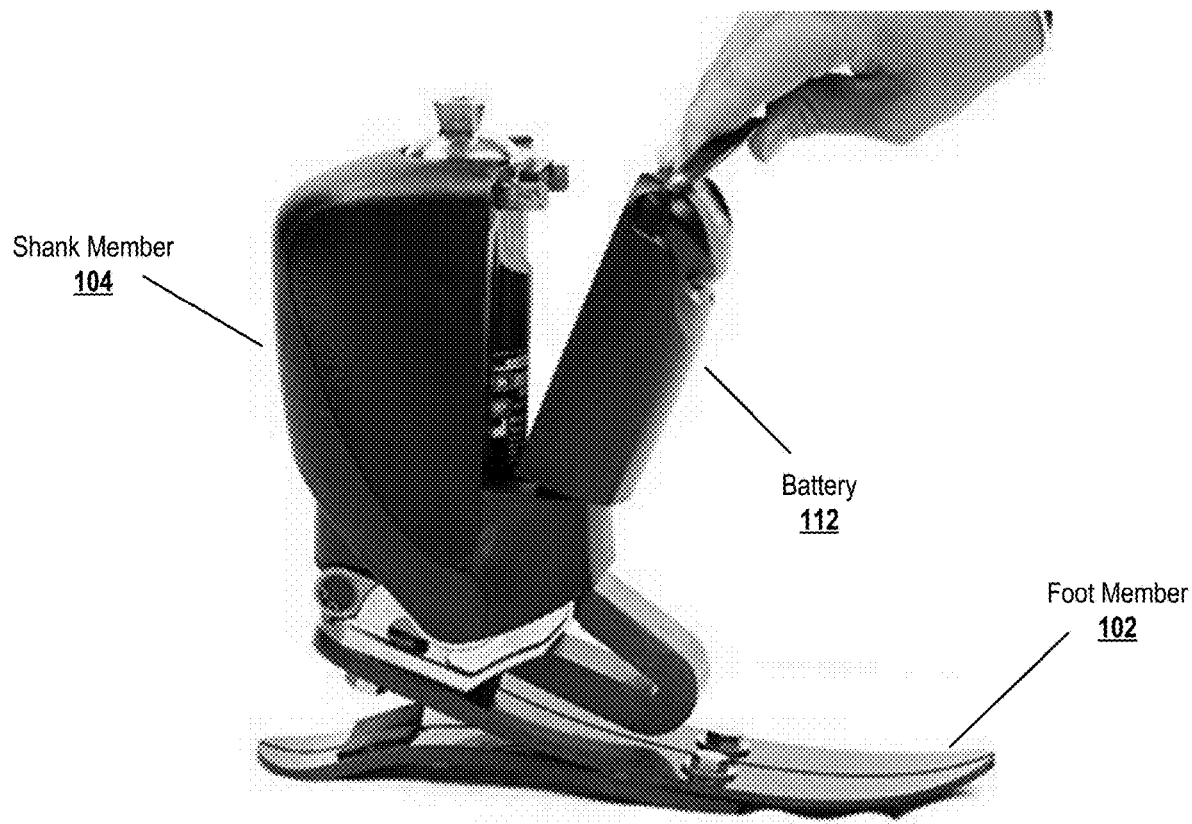
Figure 2:
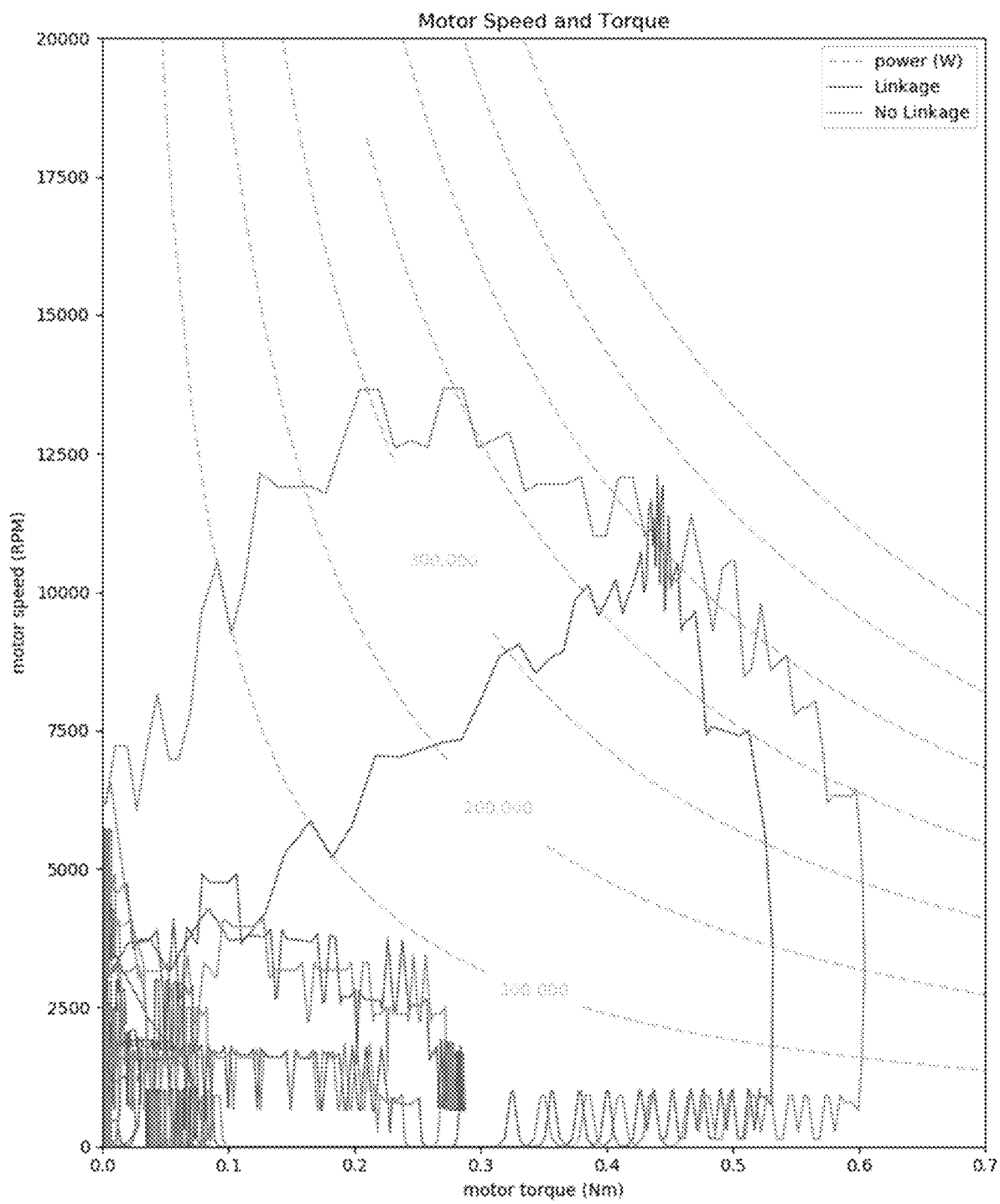
FIG. 2 depicts a graph of motor torque versus motor speed for an exemplary embodiment as compared to a no-linkage example.

One problem that arises in connection with powered augmentation devices is that the load (e.g., the motor) generally operates at a base power level, but may occasionally require relatively high power pulses. For example, FIG. 2 is a graph showing the motor speed, torque, and power used at various times during a gait cycle of exemplary ankles. As shown, the motor often operates at relatively low torque and/or speed (resulting in a relatively low power requirement), but occasionally applies bursts of increased power.

The timing of the increased power requirement may vary depending on the type of augmentation device and the device's particular application. For example, FIG. 3 is a schematic illustration of the different phases of a subject's gait cycle over level ground. The gait cycle is typically defined as beginning with the heel strike of one foot and ending at the next heel strike of the same foot. The gait cycle is broken down into two phases: the stance phase (about 60% of the gait cycle) and the subsequent swing phase (about 40% of the gait cycle). The swing phase represents the portion of the gait cycle when the foot is off the ground. The stance phase begins at heel-strike when the heel touches the ground and ends at toe-off when the same foot rises from the ground surface. The stance phase is separated into three sub-phases: Controlled Plantarflexion (CP), Controlled Dorsiflexion (CD) and Powered Plantarflexion (PP).

CP begins at heel-strike illustrated at 302 and ends at foot-flat at 306. CP describes the process by which the heel and forefoot initially make contact with the ground. Researchers have shown that CP ankle joint behavior is consistent with a linear spring response where joint torque is proportional to the displacement of the joint in relation to an equilibrium position of the joint position. The spring behavior is, however, variable; joint stiffness is continuously modulated by the body from step to step within the three sub-phases of stance and late swing state.

After the CP period, the CD phase continues until the ankle reaches a state of maximum dorsiflexion and begins powered plantarflexion PP as illustrated at 310. Ankle torque versus position during the CD period is described as a nonlinear spring where stiffness increases with increasing dorsiflexion. A prosthetic or orthotic foot or ankle-foot device may have elastic elements in the form of energy storing distal plate(s) or a series or parallel spring located within the foot or ankle-foot device. The ankle stores elastic energy during CD which assists to propel the body upwards and forwards during the PP phase. A powered prosthetic, orthotic, or exoskeleton device will apply positive power from an actuator to further assist propelling the body. Negative power, in the form of energy dissipation, may be utilized during the CP phase to cushion impact.

The PP phase begins after CD and ends at the instant of toe-off illustrated at 314. During PP, the ankle applies torque in accordance with a reflex response that catapults the body upward and forward. The catapult energy is then released along with the spring energy stored during the CD phase to achieve high plantarflexion power during late stance. This catapult behavior is necessary because the work generated during PP is more than the negative work absorbed during the CP and CD phases for moderate to fast walking speeds. The foot is lifted off the ground during the swing phase, from toe-off at 314 until the next heel strike at 318.

Powered human augmentation devices may seek to mimic the behavior of a natural human ankle joint. To that end, the actuator of the augmentation device may move the ankle joint in accordance with the functions described in FIG. 3, which may vary depending on the stage of the gait cycle that the user is in. A battery may be employed in order to power the actuator through this cycle.

The present inventors have identified that a nominal amount of power is used in the CP, CD, ES, and LS stages. However, as the user pushes off from the ground during the PP stage, an increased amount of power is demanded in order to ensure that the user experiences biomimetic movement (to mimic natural walking) and to support and augment the user's limbs to increase the user's natural physical abilities.

In order to accommodate the increased power draw, the conventional solution is to employ a large battery capable of providing the base power level and also capable of meeting the high power demands of the load. However, providing a larger battery increases the size and weight of the augmentation device, which may be undesirable for a device that must be worn by a user for long periods of time.

A battery-powered portable device, such as a powered prosthetic or orthotic device, has a supply voltage and power limited by the design of the battery pack. The number of series cells in the battery pack determines the maximum output voltage of the pack. If the application requires higher voltage or power, one possible solution is to increase the number of cells in the battery pack.

In order to generate a higher output voltage, a voltage boost converter could also be used. The boost converter may have a non-isolated or an isolated topology. However, at high currents encountered in pulse power applications the efficiency of the boost converter circuit suffers. Due to this efficiency reduction, the overall efficiency of the system is lower, which could lower the runtime of a powered prosthetic or orthotic device. Moreover, components such as inductors and transformers required for the boost converter design introduce size and weight penalties on the system.

In order to address these issues, exemplary embodiments described herein relate to a supplementary power module for a powered augmentation device. The power module provides short, periodic boost of voltage and power to an electrical motor drive for an actuator of the device. The greater electrical power is translated to greater mechanical power, thus enabling device to perform more strenuous work.

The exemplary power module makes use of a supercapacitor as an energy storage and release element. The energy in the supercapacitor is released in short, high power pulses when required by the actuator. The energy in the supercapacitor is restored when the load power is low or nominal, such as between user steps during the swing phase of the gait cycle (in the case of a powered prosthetic ankle). A logic controller drives electronic switches that facilitate the charge and discharge behavior in the supercapacitor. Exemplary embodiments may reduce the mechanical size and weight of the device's power source (such as a battery) and improve the device's ability to quickly satisfy extra power demand by the electrical load.

According to one aspect, the circuit restricts power from backflowing from the motor into the supercapacitor in order to charge the supercapacitor (e.g., by not providing a charging path from the motor back to the supercapacitor). Instead, the supercapacitor is solely charged by the battery during periods at which the battery can supply more power than the load demands, which reduces the cost, size, weight, and complexity of the system.

Although exemplary embodiments are described in connection with a prosthetic ankle that requires surges of power during a normal walking gait, the principles described herein can be readily applied to ankle devices used in other applications (e.g., running, climbing stairs, descending a ramp, walking on a slick surface, etc.) and to other types of devices (prosthetic arms, knees, hips, etc.; powered exoskeletons; powered orthotic devices; etc.). Any such device that operates on electrical power and applies surges or power augmentations may make use of the techniques described herein. For example, the device might apply augmented power in a repeated cycle, as might be done in a prosthetic ankle used in a walking gait, or in isolated circumstances, such as an arm and/or shoulder joint required to occasionally lift a heavy weight.

Figure 5:
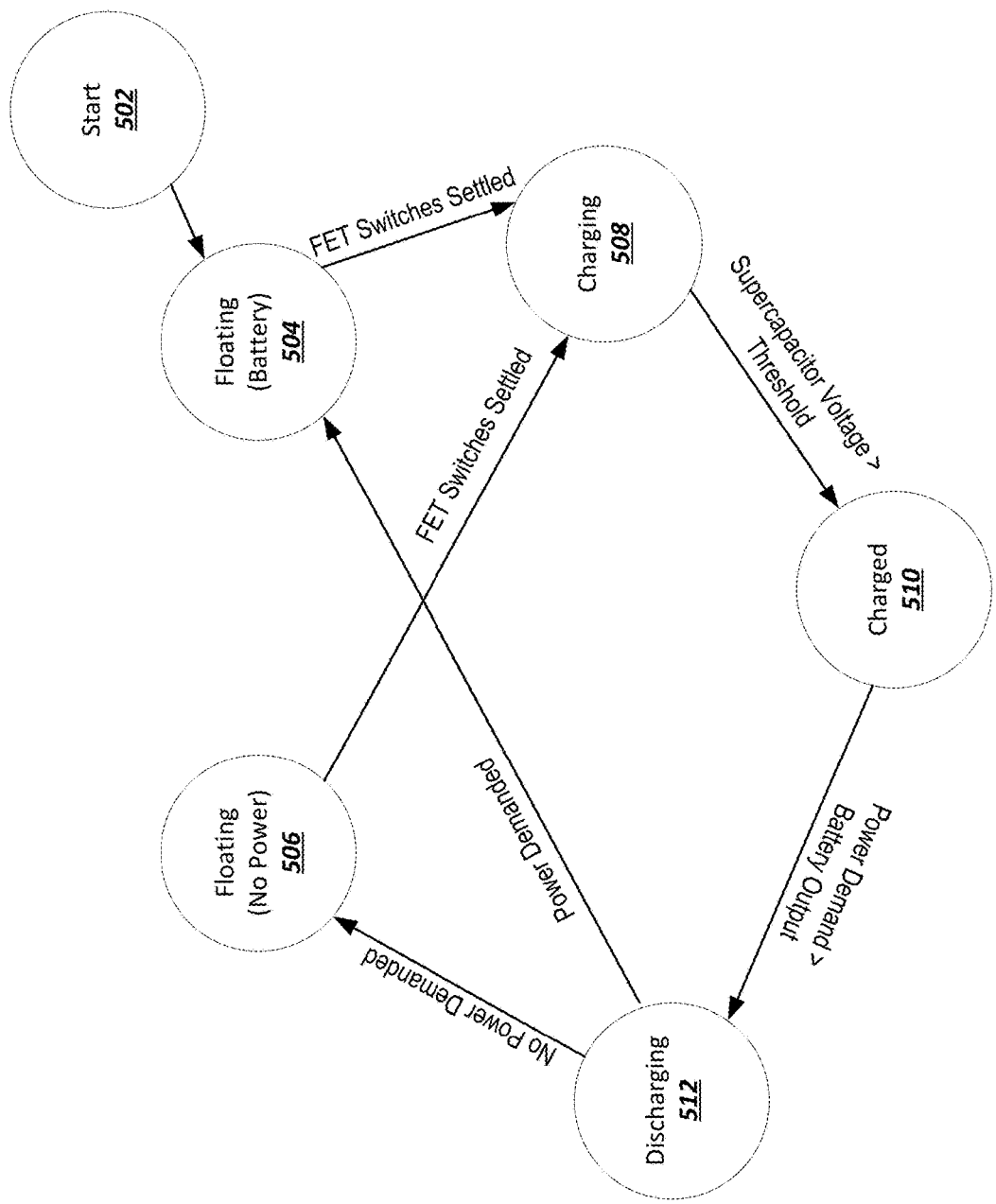
FIG. 5 is a state diagram depicting exemplary states and transitions suitable for use with exemplary embodiments.
Figure 6:
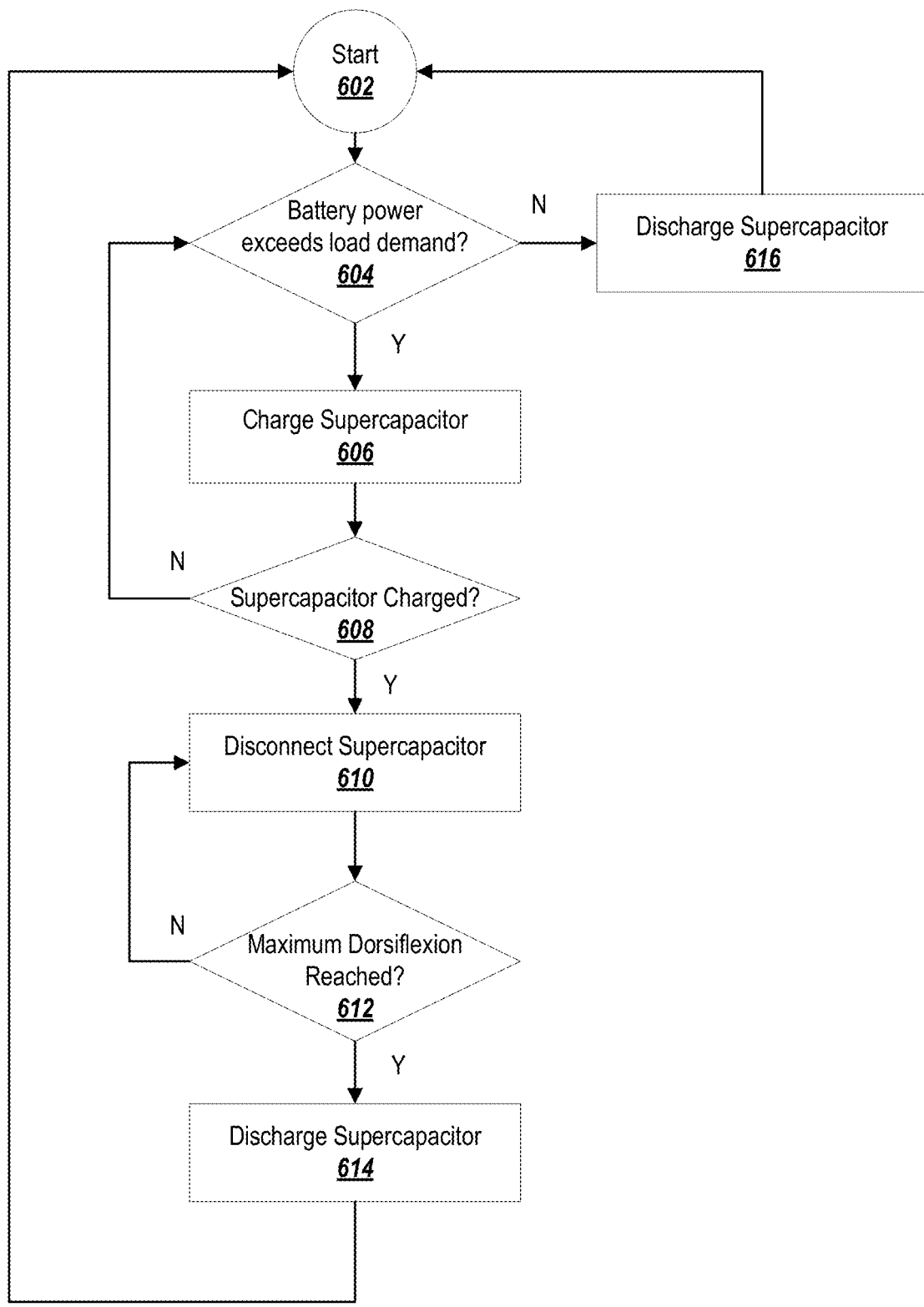
FIG. 6 is a flowchart describing an exemplary logic flow suitable for practicing exemplary embodiments.

To adapt the techniques described herein to other applications, all that would be required is that the circumstances surrounding the peak power demand from the load be identified, and the state diagram of FIG. 6 be adapted to the peak power timing. The general circuit structure shown in FIG. 5 may be used directly or adapted in minor ways depending on the application.

Moreover, although the augmentation device described herein is associated with a single anatomical joint (an ankle joint), one of ordinary skill in the art will recognize that the invention may also apply to one or more joints of a multi-joint augmentation device, such as a walking exoskeleton, a knee-ankle-foot prosthesis, or an orthosis.

Figure 4:
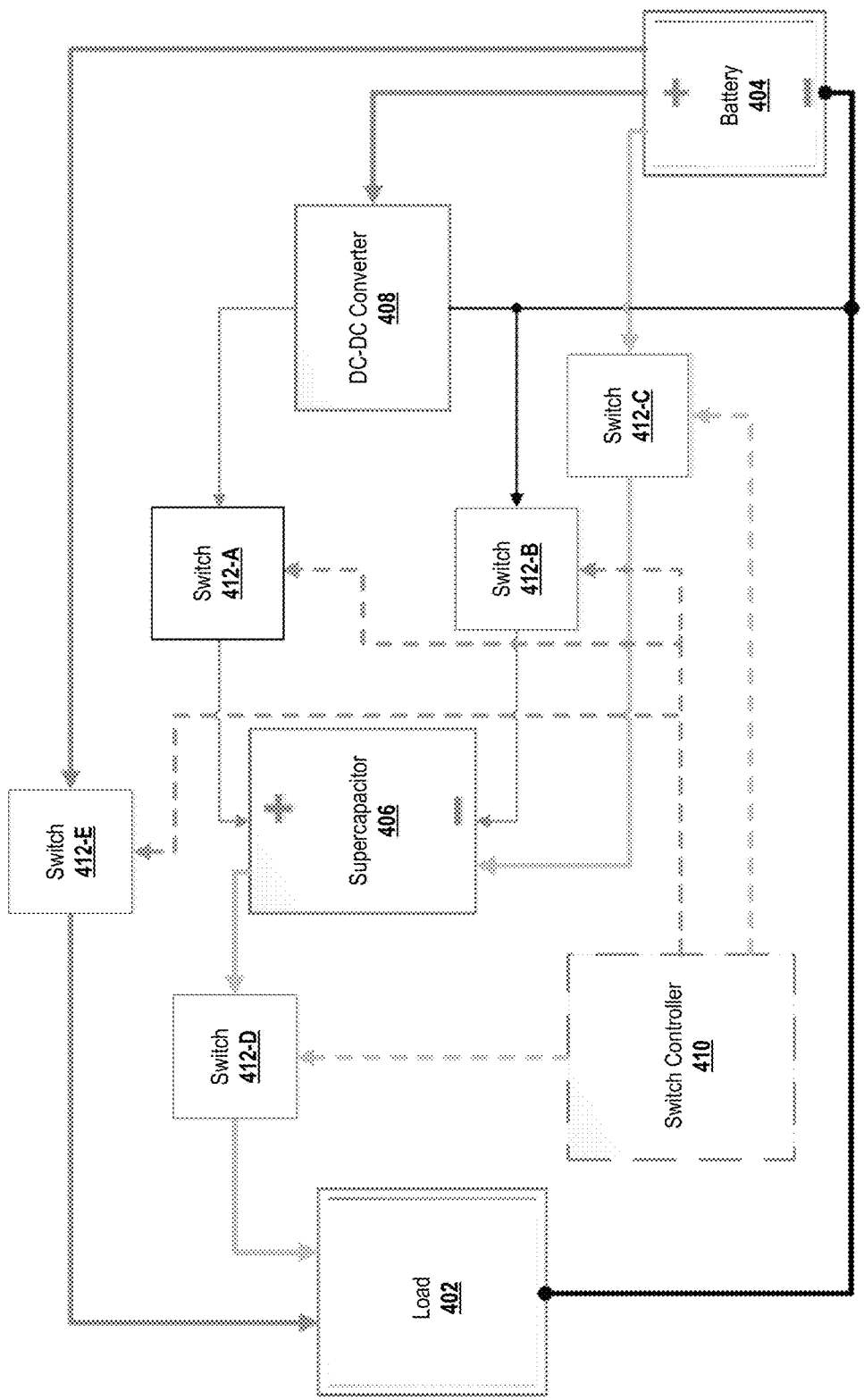
FIG. 4 is a block diagram depicting a circuit suitable for use in exemplary embodiments.

FIG. 4 is a block diagram depicting a circuit suitable for use in exemplary embodiments.

For a powered prosthetic or orthotic device application, the load 402 of the circuit is typically a motor driver and circuit that draws high power pulses periodically during use of the device. The primary input power source to the load 402 may be a portable battery system 404, or any other suitable power source.

The load 402 to the circuit may be an actuator motor that demands pulses of high power during the actuation cycle. In exemplary embodiments, these pulses are provided by a supercapacitor 406. The supercapacitor 406 represents an energy storage element that rapidly discharges its energy and provides a burst of high power when required by the load 402. It is rated for a large number of charge and discharge cycles.

Thus, the high power demand by the load 402 is partially fulfilled by the supercapacitor 406. However, the nominal power draw of the system may be low, and the supercapacitor 406 may be disconnected from the load circuit when the high power pulse is not needed.

When the supercapacitor 406 energy is depleted, it may be connected to the battery 404 and replenished during the gap between high power pulses. To that end, the battery 404 may connect to a DC-DC converter 408 that converts the voltage of the battery 404 (or other main power) into a voltage level suitable for charging the supercapacitor 406. The power supply may be a battery pack consisting of multiple battery cells in series and the voltage of the battery pack may exceed the voltage needs of a supercapacitor. The DC-DC converter 408 charges the supercapacitor 406 at a constant rate. The output current of the DC-DC converter 408, which is the charging current of the supercapacitor 406, is regulated at a fixed value. The higher the value of the current, the faster the supercapacitor 406 completes charging.

To allow the circuit to be reconfigured to support these different states (nominal power draw supplied by battery 404, high power burst supplied by the battery 404 and the supercapacitor 406, recharging the supercapacitor 406 from the battery 404, etc.), a number of discrete semiconductor switches 412-A, 412-B, 412-C, 412-D, 412-E may be provided (the switches may be field-effect transistor, or FET, switches).

Among other responsibilities, the switches 412 connect the supercapacitor 406 in either charging mode or discharging mode, but not both simultaneously. When the supercapacitor is charging, a switch 412-E connects the battery 404 directly to the load so that power to the load continues uninterrupted.

In particular, a first switch 412-A connects the positive output of the DC-DC converter 408 to the supercapacitor 406. A second switch 412-B connects the negative output of the DC-DC converter 408 to the supercapacitor 406. When the switches 412-A and 412-B are ON, the supercapacitor 406 is charging.

A third switch 412-C connects the positive output of the DC-DC converter 409 to the supercapacitor 406 negative pin. A fourth switch 412-D connects the supercapacitor 406 positive pin to the high side of the load 402. When the switches 412-C and 412-D are ON, the series combination of two voltage sources (i.e. the battery 404 and the supercapacitor 406) is connected to the load 402. The effective voltage supplied to the load 402 is the sum of the battery 404 voltage and the supercapacitor 406 voltage.

A fifth switch 412-E connects the positive of the battery 404 output to the load 402 high side.

The low side of the load 402 is always connected to the negative of the battery 404 output.

A controller 410 opens and closes the switches depending on the desired state of the circuit. To that end, the controller 410 may maintain a state diagram, such as the one depicted in FIG. 5, and may change the switches 412-A-412-E based on the desired state of the system. Each state may be associated with a unique combination of switches. The operation of the controller 410 enables the supercapacitor 406 to be charged to the required voltage and then placed in series with the battery 404 at the appropriate time when a voltage/power boost is needed. The controller 410 monitors the load 402 requirements and changes states in response to the monitored signals. The controller 410 also allows the supercapacitor 406 charge to be replenished after a discharge. This cycle repeats in response to demand for voltage/power boost from the load 402.

With reference to the exemplary state diagram depicted in FIG. 5, the system may begin in a start state 502, after which the system temporarily transitions into a floating (battery) state 504. In the floating (battery) state 504, the supercapacitor is floating (neither being charged nor discharged) and the load is powered by the battery. Alternatively, the system may begin in the floating (no power) state 506. In this state, neither the battery nor the supercapacitor is attached to the load, and so the load draws no power. The floating (battery) state 504 and the floating (no power) state 506 serve as a transition states between periods when the supercapacitor is being charged or discharged. These states are intended to allow the FET switches to settle in a fully on or fully off state before being adjusted.

If the battery supplies more power than is needed by the load, the system can be placed in the charging state 508. In some embodiments, the power supplied by the battery must exceed that required by the load by more than a certain threshold amount before placing the system in the charging state 508. In this state, the battery continues to supply power to the load, but also connects to the supercapacitor via the DC-DC converter in order to charge the supercapacitor.

The system may remain in the charging state, allowing any excess power provided by the battery to recharge the supercapacitor, until the supercapacitor becomes charged (e.g., when the supercapacitor voltage exceeds a "charged" threshold). At this point, the system moves into the charged state 510.

If, while the supercapacitor is in the charged state, the power demanded by the load exceeds the power supplied by the battery, the supercapacitor and the battery may be connected in series and the system may be placed in the discharging state 512. After the peak power demand is reduced, the system may temporarily transition into one of the floating (no power) state 506, the floating (battery) state 504 before transitioning into the charging state 508.

In an embodiment focused on a powered ankle device, peak power tends to be demanded during the powered plantarflexion (PP) stage of the gait cycle. Accordingly, the system may transition from the charged state 510 to the discharging state 512 in response to detecting that the ankle device is about to enter the PP stage. This generally occurs as the ankle joint approaches its point of maximum dorsiflexion. The system may detect this occurrence in several ways.

In some embodiments, the ankle joint, shank member, and/or foot member may be provided with one or more sensors that detect an angle of the shank member with respect to the foot member. The device may be associated with a maximum amount of dorsiflexion, which may be personalized to a given user (e.g., based on historical user data that indicates that the user tends to cease dorsiflexion at a particular angle) and/or may be enforced by mechanical or other means (such as a hard stop that prevents the foot member from rotating past a certain point). Based on readings from the sensors, the system calculates an angle associated with the ankle joint and may determine if a point of maximum dorsiflexion has been reached (or if the ankle angle is within a predetermined amount of the angle that would indicate maximum dorsiflexion, indicating that maximum dorsiflexion is imminent).

In other embodiments, rather than relying on angle measurements of the ankle, the system may rely on a sensor configured to detect whether the aforementioned hard stop has been reached (or is approached to within a predetermined threshold range). If so, the system may determine that maximum dorsiflexion is, or is about to be, reached.

The system may leave the discharging state 512 at the end of powered plantarflexion, which may be detected based on angular measurements and/or by sensing the occurrence of the toe of the foot member leaving the ground ("toe-off"). Alternatively, power may be applied for a set or calculated time, after which the system is transitioned to a floating or charging state.

Note that more or different transitions may be possible than the ones shown in FIG. 5. Similarly, other configurations of the state chart are possible. In one, the system may transition between the floating states 504, 506, the charging state 508, and the discharging state 512, but may not have a separate charged state 510. Instead, the system may maintain a flag or other parameter indicating when the supercapacitor is fully charged (or may store the voltage level of the supercapacitor for comparison against a threshold). If the system is in the charging state 508 when a surge of power is demanded, the system may condition transitioning to the discharging state 512 on whether the supercapacitor is already charged; if not, the system may remain in the charging stat 508 and supply the power from the battery. Alternatively, the system could transition to the discharging state 512 without regard to the charge status of the supercapacitor, allowing the supercapacitor to supply the load with whatever power it is capable of, given its current charge level.

With reference again to the circuit diagram of FIG. 4, it will now be understood that the states described above can correspond to a particular configuration of the switches 412-A-412-E, as shown in Table 1 below.

TABLE 1

| Condition of Switches | State of the supercapacitor | Power source for the load |
| --- | --- | --- |
| A, B, E<br>C, D | ON<br>OFF | Charging | Battery |
| A, B, E<br>C, D | OFF<br>ON | Discharging | Supercapacitor, Battery (Series Combination) |
| A, B, C, D<br>E | OFF<br>ON | Floating | Battery |
| A, B, C, D, E | OFF | Floating | No power |

The controller 410 may maintain a state diagram such as the one depicted in FIG. 5, and may adjust the switches as shown in Table 1 based on the state into which the system is transitioning.

To provide a particular example, FIG. 6 is a flowchart describing an exemplary logic flow 600 suitable for practicing an exemplary embodiments in the form of a powered ankle. The logic flow 600 may be embodied as instructions stored on a non-transitory computer-readable medium, and executed by one or more processors (such as the above-described controller) of a system.

Processing may start at block 602. At block 604, the system may determine if the amount of power that the battery is capable of supplying exceeds the power demanded by the load. If not, processing proceeds to block 616, where the supercapacitor is temporarily floated and then connected to the load and discharged to provide supplemental power. To this end, the controller may adjust the switches to correspond to the discharging state as shown in Table 1, potentially with a transition to either the floating (battery) or floating (no power) state. Alternatively, if the supercapacitor does not have sufficient charge, then the load may be run off the battery with reduced functionality in order to allow the supercapacitor to fully charge. Processing then returns to block 602 (potentially after waiting a predetermined period of time).

When the battery power does exceed the load demand at block 604, processing may proceed to block 606 and the supercapacitor may be charged. The controller may adjust the switches to correspond to the charging state as shown in Table 1, potentially after temporarily placing the supercapacitor into one of the floating states until the FET switches have an opportunity to settle in the on or off state.

Processing may optionally delay for a predetermined period of time, and then proceed to block 608 where it is determined if the supercapacitor has reached full charge. In block 608, the voltage level of the supercapacitor may be compared to a predetermined threshold level to determine whether the supercapacitor is charged. If not, processing may return to block 604, where the system determines if the supercapacitor can continue charging or if the supercapacitor should be floated.

If the supercapacitor is determined to be charged at block 608, then processing may proceed to block 610, where the supercapacitor is disconnected from the DC-DC converter. Alternatively, the supercapacitor may remain connected to the DC-DC converter, without regard to whether it is fully charged.

At block 612, the system may determine if the foot member has reached maximum dorsiflexion (or is about to reach maximum dorsiflexion, such as when the measurements described above are within a predetermined threshold amount of the value that would indicate maximum dorsiflexion). This may be achieved, as discussed above, based on angle sensors, hard stop sensors, or other techniques. If the determination at block 612 is "no," then processing may return to block 610. Otherwise, processing proceeds to block 614 and the system discharges the supercapacitor.

To this end, the supercapacitor and the battery may be connected in series to provide power to the load. The controller may accordingly adjust the switches to correspond to the "discharging" state in Table 1.

After the supercapacitor is discharged, the supercapacitor may be temporarily placed into one of the float states from Table 1. Processing may then return to block 602, and the procedure may begin again for a new gait cycle.

Ideally, the amount of power that the supercapacitor captures from the battery through a single gait cycle will be sufficient to meet the increased power demand during powered plantarflexion (or other period of increased power demand, depending on the application). If there is insufficient power to fully charge the supercapacitor, different embodiments may be used. In one embodiment, the supercapacitor may be discharged when increased power is demanded, although the supercapacitor may not be capable of providing the full amount of the increased power demand. In another embodiment, the system may refrain from discharging the supercapacitor to allow the supercapacitor to fully recharge for a future cycle.

Although exemplary embodiments are generally described herein, for illustration purposes, with respect to a powered ankle joint prosthesis, one of ordinary skill in the art will recognize that the present invention is not so limited. The described supercapacitor may also be employed in connection with other joints, such as knees, elbows, hips, etc., and may be employed in connection with other powered augmentation devices, such as orthoses, exoskeletons, etc.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A powered augmentation device comprising:
   a electrical load;
   a battery configured to supply power to the load;
   a supercapacitor;
   an electrical circuit connecting the battery, the supercapacitor, and the load, wherein the electrical circuit is configurable in at least:
      a first configuration in which the battery and the supercapacitor jointly supply power to the load during a repeating phase of a gait cycle of the powered augmentation device, and
      a second configuration in which the battery supplies power to the load and recharges the supercapacitor;
   a hardware controller configured to monitor signals indicative of requirements on the load, and to switch the electrical circuit between the first configuration and the second configuration in response to the monitored signals.

2. The powered augmentation device of claim 1, wherein the load is configured to alternate between a nominal power draw and receiving pulses of high power throughout the gait cycle, and the supercapacitor is configured to provide the pulses of high power.

3. The powered augmentation device of claim 1, wherein the supercapacitor is configured to provide 6 Joules of energy in less than 300 ms.

4. The powered augmentation device of claim 1, further comprising a DC/DC converter configured to convert a source voltage from the battery into a voltage level suitable for charging the supercapacitor.

5. The powered augmentation device of claim 1, further comprising a plurality of FET switches, wherein the controller is configured to switch the electrical circuit between the first configuration and the second configuration by adjusting the FET switches.

6. The powered augmentation device of claim 1, wherein the controller is configured to switch the electrical circuit between the first configuration and the second configuration in a period of time while the load is disconnected from the electrical circuit.

7. The powered augmentation device of claim 1, wherein the electrical circuit is configured not to provide backflow energy from the load to the supercapacitor.

8. The powered augmentation device of claim 1, wherein the device comprises an ankle, and the controller is configured to place the electrical circuit in the first or second configuration during a powered plantarflexion phase.

9. The powered augmentation device of claim 8, further comprising a sensor for detecting an angle of an ankle joint, wherein the controller is configured to place the electrical circuit in the first configuration based on a signal received from a sensor.

10. The powered augmentation device of claim 8, further comprising a hard stop, wherein the load is disconnected when the hard stop is reached.

11. The powered augmentation device of claim 8, wherein the supercapacitor is recharged between successive steps of the gait cycle.

12. The powered augmentation device of claim 1, wherein the device comprises a knee.

* * * * *